United States Patent [19]

Morrison, Jr. et al.

[11] 4,409,253

[45] Oct. 11, 1983

[54] RECOVERY OF NONCAFFEINE SOLUBLES IN AN EXTRACT DECAFFEINATION PROCESS

[75] Inventors: Lowen R. Morrison, Jr., Hamilton, Ohio; Melisse N. Elder, Villa Hills, Ky.; John H. Phillips, Fairfield, Ohio

[73] Assignee: The Procter & Gamble Company, Cincinnati, Ohio

[21] Appl. No.: 411,752

[22] Filed: Aug. 26, 1982

Related U.S. Application Data

[63] Continuation of Ser. No. 240,730, Mar. 5, 1981, abandoned.

[51] Int. Cl.$^3$ .............................................. A23F 5/22
[52] U.S. Cl. .................................... 426/424; 426/427; 426/428
[58] Field of Search ..................... 426/424, 427, 428

[56] References Cited

U.S. PATENT DOCUMENTS

| | | | |
|---|---|---|---|
| 1,123,827 | 1/1915 | Whitaker et al. ................ | 426/428 X |
| 2,472,881 | 6/1949 | Bender ............................ | 426/427 X |
| 2,508,545 | 5/1950 | Shuman ........................... | 426/428 X |
| 4,031,251 | 6/1977 | Margolis ......................... | 426/427 X |

FOREIGN PATENT DOCUMENTS 865488 10/1978 Belgium.

OTHER PUBLICATIONS

Sivetz, Coffee Processing Technology, 1963, Avi: Westport, Conn., pp. 207–214.

Primary Examiner—Joseph M. Golian
Attorney, Agent, or Firm—Eric W. Guttag; Michael J. Roth; Richard C. Witte

[57] ABSTRACT

An improved extract decaffeination process. Roast coffee extract is contacted with a water-immiscible organic solvent to form decaffeinated extract and caffeine-containing spent solvent. The spent solvent is contacted with water to form decaffeinated spent solvent and caffeine-containing spent water. The spent water can be concentrated to a caffeine content of from about 7 to about 30% by weight. The caffeine in the concentrated spent water can be crystallized out and then separated from the residual spent water. The noncaffeine solubles present in the residual spent water can then be recovered.

22 Claims, 1 Drawing Figure

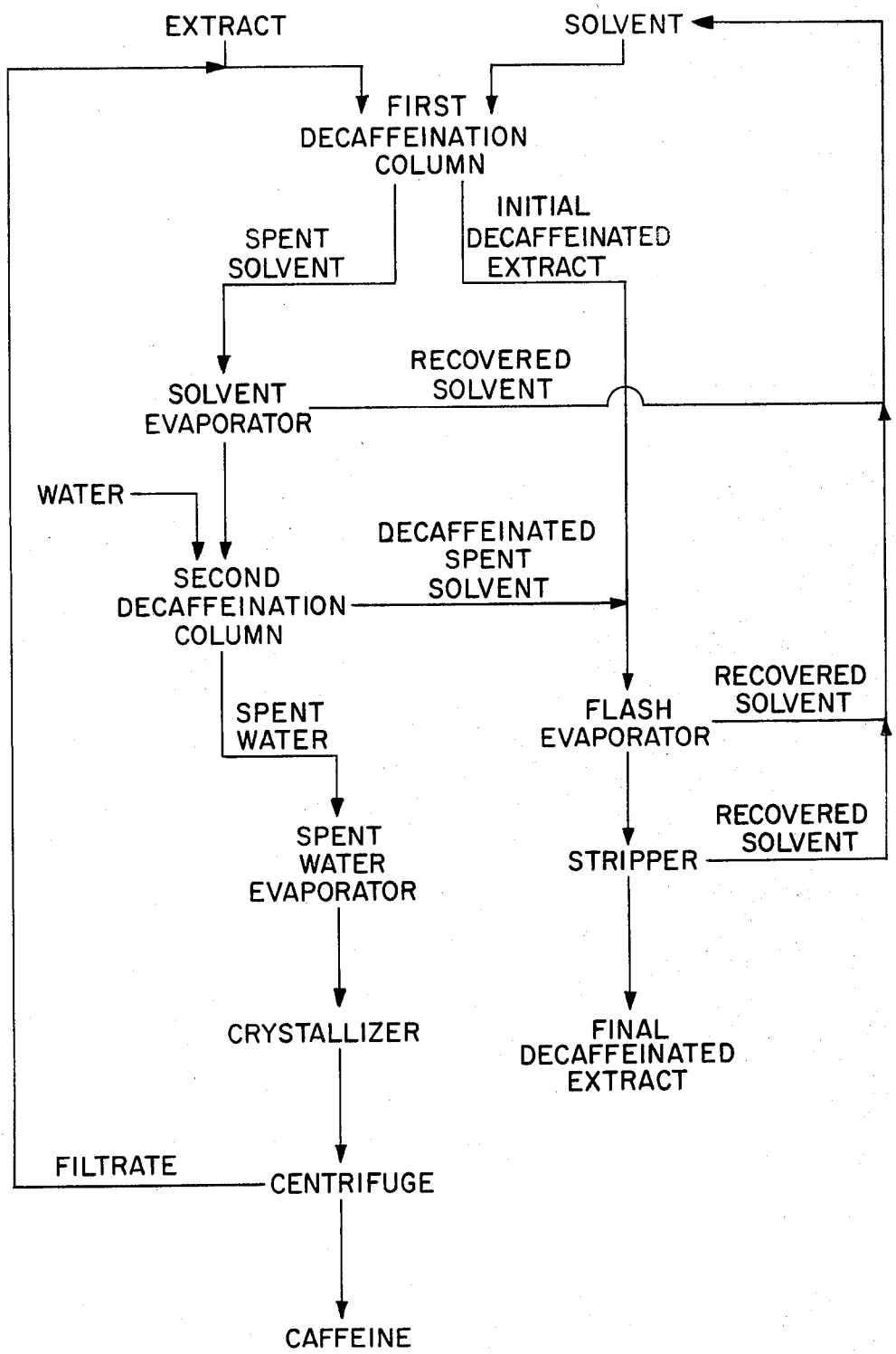

RECOVERY OF NONCAFFEINE SOLUBLES IN AN EXTRACT DECAFFEINATION PROCESS

This is a continuation of application Ser. No. 240,730, filed Mar. 5, 1981 and now abandoned.

TECHNICAL FIELD

The present invention relates to improvements in the field of extract decaffeination. In particular, the present invention relates to recovery of noncaffeine solubles in an extract decaffeination process for instant coffee.

BACKGROUND ART

A significant portion of the instant coffee market is decaffeinated instant coffee products. Several technical factors are important in the processing to form such coffee products. One factor is the effectiveness of the decaffeination process in removing caffeine from the coffee. A satisfactory process usually removes 97% or more of the caffeine from the coffee. Another factor is the efficiency of the decaffeination process in removing caffeine from the coffee. A process which is slower in decaffeinating coffee usually necessitates a large amount of capital equipment to handle commercial quantities of coffee.

The above technical factors further impact on the commercial acceptability of the decaffeination process. The decaffeination process should be economical. Factors which favor reduction in cost such as recovery of caffeine removed from the coffee are thus desirable. The decaffeination process should also provide a decaffeinated instant coffee product having a desirable flavor and aroma in terms of both quantity and quality. The quantity aspect relates to the total coffee solubles yield which can be extremely important to the cost effectiveness of the decaffeination process. The quality aspect relates to the retention of the key components which provide the aroma and flavor character of the coffee.

One method for forming decaffeinated instant coffee products involves green bean decaffeination. In one such process, green beans are prewet to increase the moisture content to upwards of 40% or more. The prewetted beans are then extracted with a water-immiscible organic solvent in a countercurrent fashion somewhat similar to that used to form coffee extract from roast and ground coffee. After decaffeination, the residual solvent is removed from the beans (desolventizing), usually by steam stripping. See U.S. Pat. No. 3,671,262 to Wolfson et al, issued June 20, 1972, and U.S. Pat. No. 3,671,263 to Patel et al, issued June 20, 1972. After stripping, the decaffeinated beans are roasted, ground and extracted as in a normal instant coffee processing system. See also U.S. Pat. No. 2,309,092 to Berry et al, issued Jan. 26, 1943, which discloses a related decaffeination process involving the formation of an aqueous extract of green coffee solubles which is decaffeinated with a water-immiscible organic solvent.

Green bean decaffeination methods are usually quite effective to remove caffeine from the coffee. However, such methods also have reduced processing efficiency. Whether the caffeine solvent is water or water-immiscible organic solvent, the mass transport mechanism for removal of caffeine from the beans is very slow. The decaffeination step usually requires several hours in order to provide effective decaffeination of the green bean. A similar statement can be made with regard to the step of desolventizing the decaffeinated beans. A green bean decaffeination process therefore more closely approximates a batch rather than a continuous decaffeination process.

Because of the reduced processing efficiency, green bean decaffeination methods can be relatively expensive. Such expense becomes especially great when commercial quantities of green coffee beans are involved. Because of the batch-like nature of the process, decaffeination of large quantities of beans increases the amount of capital equipment required, especially in the decaffeination and desolventizing steps. This capital equipment is typically quite costly. Also, a large storage and handling capacity is usually required at added cost.

There is some removal of coffee flavor and aroma compounds or precursors, especially water-insoluble waxes, during green bean decaffeination. These coffee compounds, as well as the caffeine, are desirably recovered to reduce the cost of the green bean decaffeination process and to improve the aroma and flavor quality of the decaffeinated instant coffee product. For example, solids present in the caffeine-containing organic solvent can be recovered by evaporating the solvent to dryness and extracting the solids with water. Oils and other insolubles can be separated for addback to the decaffeinated green beans. The residual aqueous phase can be concentrated and the caffeine crystallized for recovery. Alternatively, the caffeine-containing solvent can be contacted with water to recover the water solubles. The aqueous phase can then be extracted with additional caffeine solvent or evaporated to recover the caffeine. The water insolubles can be recovered from the original solvent by evaporation and/or subsequent treatment with water. See U.S. Pat. No. 3,669,679 to Panzer et al, issued June 13, 1972. See also U.S. Pat. No. 4,081,563 to Hudak et al, issued Mar. 28, 1978, wherein an aqueous extract from green coffee is dried, decaffeinated with a solvent such as ethyl acetate and the decaffeinated coffee solubles added back to the green coffee; coffee solubles present in the caffeine-rich solvent can also be recovered and added back to the decaffeinated coffee solubles.

Another method for forming decaffeinated instant coffee involves direct decaffeination of roast and ground coffee extract with a water-immiscible organic solvent. Such a decaffeination process is normally referred to as liquid-liquid extraction. In such a decaffeination process, roast and ground coffee extract is normally flowed countercurrently to the organic solvent. The solvent removes the caffeine from the coffee extract to provide a decaffeinated extract. The decaffeinated extract is stripped of residual solvent and then processed further to form a decaffeinated instant coffee product. See U.S. Pat. No. 2,933,395 to Adler et al, issued Apr. 19, 1960, which discloses a countercurrent extract decaffeination process.

Direct decaffeination of roast and ground coffee extract can be an effective and efficient method for removing caffeine from the coffee. For example, in countercurrent extract decaffeination, the coffee extract is usually dispersed in the form of small droplets through a continuous solvent phase. The small droplets present a large surface area to the solvent. Because of the large surface area, mass transfer of caffeine from the coffee extract to the solvent is significantly increased. Because of the increased mass transfer, extract decaffeination can become a truly continuous decaffeination process.

Direct decaffeination of roast and ground coffee extract can provide a less expensive decaffeination process than green bean decaffeination. The continuous nature of extract decaffeination can decrease capital equipment requirements for processing large quantities of coffee. Also, because coffee extract rather than green beans are decaffeinated, an extract decaffeination process requires less coffee bean inventory and is more flexible.

As with green bean decaffeination, the cost of an extract decaffeination process can be reduced by recovery of the caffeine. One such caffeine recovery system is disclosed in U.S. Pat. No. 2,508,545 to Shuman, issued May 23, 1950. Referring to the drawing of the Shuman patent, roast and ground coffee extract is decaffeinated in a liquid-liquid extraction column 2 with a suitable caffeine solvent such as trichlorethylene. The caffeine in the solvent is partitioned into an aqueous solution by liquid-liquid extraction. The caffeine-containing solution is concentrated at 5 to about 30% caffeine content and is then treated with carbon at 6 and 7. Alkali is added subsequent to carbon treatment to raise the pH to at least 7. The alkaline solution is water cooled and the caffeine crystallized out at 8. The crystallized caffeine is separated from the mother liquor by a centrifuge 9.

The Shuman patent indicates three different paths for further processing of the mother liquor. The first path involves return of the mother liquid to the caffeine-containing solution at 5. The second path involves concentration at 16 to about 30% caffeine content, crystallization of the caffeine at 17 and separation of the caffeine by centrifuge 18 with the residual mother liquor being discarded. The third path involves adding sulfuric acid at 20 with subsequent liquid-liquid extraction at 2A with a caffeine solvent such as trichlorethylene. The caffeine-containing solvent at 2A is combined with the caffeine-containing solvent from column 2. The residual mother liquor is discarded.

Another method for recovering caffeine obtained during decaffeination of roast and ground coffee extract is disclosed in U.S. Pat. No. 2,472,881 to Bender, issued June 14, 1949. Referring to the drawing of the Bender patent, the caffeine-containing solvent (e.g. trichloroethylene) is concentrated and then liquid-liquid extracted with water at 2. The decaffeinated solvent is recovered by evaporation at 4 with the residual water insoluble impurities being discarded. The aqueous caffeine solution which also has water soluble impurities is concentrated at 3, treated with carbon at 5 and 6 and the caffeine crystallized at 7. The crystallized caffeine is separated by a centrifuge 8 with the mother liquor ultimately liquid-liquid extracted with fresh organic solvent at 11. This caffeine-containing solvent from 11 is returned for further concentration at 1. The spent mother liquor containing water soluble impurities is discarded.

One significant problem with extract decaffeination is the loss of coffee flavor and aroma components, especially where less selective organic solvents such as ethyl acetate are utilized. An extract decaffeination process typically reduces the total coffee solubles yield. For example, after extract decaffeination, it has been found that a less selective organic solvent such as ethyl acetate contains a mixture of coffee solids, liquids and hard to define amorphous materials (hereinafter noncaffeine solubles) typically in a ratio to caffeine of approximately 2:1 by weight. These noncaffeine solubles also contain some of the key aroma and flavor components found to be missing from decaffeinated instant coffee products.

Only recently has concern been directed at the recovery of these important noncaffeine solubles in an extract decaffeination process. One such process is described in Belgium Pat. No. 865,488 to Bolt et al, issued Oct. 2, 1978. In the Bolt et al patent, the organic caffeine-containing solvent is extracted with water to form a caffeine-containing aqueous phase and a decaffeinated solvent phase. The decaffeinated solvent phase is combined with the decaffeinated extract. Typically, this solvent/decaffeinated extract mixture is sent to a flash evaporator to remove some of the solvent. The partially desolventized mixture is then sent to an extract stripper to remove the remainder of the residual solvent. The desolventized decaffeinated extract is then processed further to provide a decaffeinated instant coffee product.

The aqueous caffeine-containing phase separated from the decaffeinated solvent phase in the process of the Bolt et al Patent Document is normally referred to as spent water. It has been found that this spent water also contains noncaffeine solubles. For ethyl acetate as the solvent, the ratio of noncaffeine solubles to caffeine is approximtely 1:1 by weight. As noted previously, the caffeine recovery systems of the Shuman and Bender patents treat these noncaffeine solubles as "impurities". These "impurities" are ultimately discarded by the systems of both the Shuman and Bender patents. However, it has been found that the recovery of these noncaffeine solubles can significantly increase the total yield of decaffeinated instant coffee. Further, it has been found that these noncaffeine solubles contain important flavor and aroma components which are normally absent from decaffeinated instant coffee products formed by an extract decaffeination process.

It is therefore an object of the present invention to decrease the cost of an extract decaffeination process.

It is another object of the present invention to recover important coffee aroma and flavor components normally lost in an extract decaffeination process.

It is a further object of the present invention to increase the total coffee solubles yield of an extract decaffeination process.

It is yet another object of the present invention to recover caffeine as valuable by-product from an extract decaffeination process.

It is yet a further object of the present invention to recover important noncaffeine solubles while at the same time recovering caffeine.

These and other objects of the present invention are disclosed hereinafter.

DISCLOSURE OF THE INVENTION

Summary of the Invention

The present invention relates to improvements in an extract decaffeination process. The decaffeination process includes contacting roast coffee extract with a water-immiscible organic solvent to form a decaffeinated extract. Also formed is a caffeine-containing solvent phase which is normally referred to as spent solvent. This spent solvent is contacted with water to form an aqueous caffeine-containing phase normally referred to as a spent water. Also formed is a decaffeinated solvent phase normally referred to as decaffeinated spent solvent.

An important aspect of the improved decaffeination process of the present invention is the recovery of caffeine as a valuable by-product from the spent water.

The spent water is usually concentrated to a caffeine content of from about 7 to about 30% by weight. The caffeine in the spent water is solidified and then separated from the residual aqueous phase of spent water. This residual spent water is normally referred to as the filtrate.

Another important aspect of the improved decaffeination process of the present invention is the recovery of noncaffeine solubles from this filtrate or residual spent water. These noncaffeine solubles are typically added back to coffee extract to be decaffeinated. The recovery of noncaffeine solubles from the residual spent water is particularly useful in conjunction with the process described in the Bolt et al patent wherein noncaffeine solubles present in the decaffeinated spent solvent are eventually added back to the decaffeinated extract. The addition of noncaffeine solubles from the residual spent water to the coffee extract to be decaffeinated, in combination with the recovery process of the Bolt et al patent, insures the eventual return of most of the noncaffeine solubles to the decaffeinated extract. This decaffeinated extract is further processed to form a decaffeinated instant coffee product.

The improved decaffeination process of the present invention has a number of significant advantages. One advantage is decreased cost of an extract decaffeination process. Caffeine is recovered as a valuable by-product from the spent water. At least about 50% by weight and typically from about 60 to about 70% by weight of the caffeine present in the spent water can be removed by the improved decaffeination process of the present invention. When the filtrate is added back to the coffee extract to be decaffeinated, a total of about 90% or more of the caffeine in the entire decaffeination system can be recovered.

Another advantage is that about 80% or more of the noncaffeine solubles present in the spent water can be removed. These recovered noncaffeine solubles significantly increase the total yield of decaffeinated instant coffee from an extract decaffeination process, especially where a less selective solvent such as ethyl acetate is used. The recovery of these noncaffeine solubles also insures retention of components important to the aroma and flavor character of a decaffeinated instant coffee product. These components are normally lost when the residual spent water is discarded as in the prior art caffeine recovery systems of the Shuman and Bender patents. The total result is a decaffeinated instant coffee product having improved flavor and aroma at a lower cost.

Formation of Roast Coffee Extract

Roast coffee extract which is suitable for instant coffee processing is usually suitable for an extract decaffeination process. As used herein, the term "roast coffee extract" includes coffee extract formed from roasted beans or roast and ground coffee. In forming roast coffee extract, various grades of green coffee beans are blended together. After blending, the green beans are roasted to a suitable roast color. The roasted beans are usually ground to a suitable state of subdivision for extraction. Typically, the roasted beans are ground to a coarse grind size.

A number of art-recognized techniques can be used for extracting the roast and ground coffee. Typically, the roast and ground coffee is placed in a series of extraction columns. The columns of coffee are then extracted in a countercurrent fashion by the passage of fresh extraction water from the most extracted columns to the least extracted columns. See U.S. Pat. No. 3,700,463 to Bolt et al, issued Oct. 24, 1972, and U.S. Pat. No. 3,700,466 to Bergeron et al, issued Oct. 24, 1972, which disclose suitable techniques, including countercurrent extraction, for forming roast coffee extract. The roast coffee extract drawn off from the columns normally has a concentration of coffee solubles of from about 15% to about 35% by weight. However, coffee extracts having greater or lesser concentrations of such coffee solubles can also be utilized.

The roast coffee extract can be volatile stripped (devolatilized) prior to the extract decaffeination step. For example, coffee extract can be devolatilized by flashing off aroma and flavor volatiles at subatmospheric pressure or by passing an inert gas such as carbon dioxide, nitrogen or steam through the coffee extract. A preferred devolatilization step involves stripping volatiles from the coffee extract with the aid of steam. The stripped volatiles are condensed usually by chilling in a suitable condenser. The condensed volatiles are later added back to the decaffeinated extract for aroma and flavor improvement in the ultimately formed decaffeinated instant coffee product.

Decaffeination of Coffee Extract

The roast coffee extract can be decaffeinated by a variety of art-recognized techniques. Generally, extract decaffeination involves the liquid-liquid extraction wherein the aqueous coffee extract is contacted with a water-immiscible organic solvent to remove caffeine from the coffee extract. As used herein, the term "water-immiscible organic solvent" refers to those solvents for caffeine which do not form homogeneous mixtures with coffee extract. A variety of water-immiscible organic solvents can be utilized in extract decaffeination. These solvents are typically divided into halogenated and nonhalogenated categories. Examples of suitable halogenated solvents include chloroform, methylene chloride, dichloroethylene, trichloroethylene, difluoromonochloromethane, and the like. Suitable nonhalogenated solvents include ethyl acetate, benzyl alcohol (alone or usually in combination with a benzyl alcohol thinner such as cyclopentane, cyclohexane or xylene), benzene and toluene.

Extract decaffeination is preferably conducted while using as low a solvent-to-coffee extract ratio as practicable. Utilization of low solvent-to-extract ratios permits removal of caffeine from the coffee extract while minimizing the amount of noncaffeine solubles removed. By decreasing the amount of solvent in contact with the extract, the extraction of noncaffeine solubles having solvent-to-water distribution coefficients smaller than caffeine is minimized. A ratio of solvent-to-coffee extract in the range of from about 0.3:1 to about 10:1 by weight can be employed. The particular ratio utilized will depend upon the particular solvent selected for extract decaffeination. For example, a halogenated solvent such as methylene chloride has a preferred ratio of from about 0.5:1 to about 1:1 by weight. In the case of a nonhalogenated solvent such as ethyl acetate, the preferred ratio ranges from about 1.4:1 to about 2:1 by weight.

Extract decaffeination can be conducted in a batch or continuous fashion. From an economics standpoint, a continuous countercurrent extract decaffeination process is preferred. Countercurrent extract decaffeination techniques are well known in the art. These techniques generally involve continuous contact of the coffee extract with the water-immiscible organic solvent, usually in an elongated column. For example, where the solvent is heavier than the aqueous roast coffee extract, the extract is introduced into the lower end of the column while the solvent is introduced into the upper end of the column. The extract travels upwardly as small dispersed droplets countercurrent to the continuous solvent phase. The decaffeinated extract is removed continuously from the top of the column while the caffeine-containing spent solvent is removed from the bottom of the column. See U.S. Pat. No. 2,933,395 to Adler et al, issued Apr. 19, 1960, which discloses a countercurrent extract decaffeination process. A version of such a decaffeination process involves passing the coffee extract countercurrently through the organic solvent in a packed columnar bed. This packed bed is in the form of an elongated tower fitted with Pall rings, Raschig rings or the like.

Preferred columns for conducting extract decaffeination include such liquid-liquid contacting devices as Rotary-Disc contactors, Oldshue-Rushton columns, or York-Scheibel columns. It will be appreciated that the feasibility of utilizing low solvent-to-extract ratios depends in part upon the nature of the solvent employed, the concentration of the coffee extract, and the efficiency or mass transfer capability of the liquid-liquid contacting device. It is preferred to employ a liquid-liquid contacting device which provides the mechanical agitation and turbulence necessary for maximum mass transfer of caffeine from the coffee extract to the solvent without excessive emulsion formation. Suitable liquid-liquid contacting devices are described in detail in Perry's Chemical Engineer's Handbook (McGraw-Hill Book Co., 4th Ed.) § 21, pp. 23-35.

Recovery of Caffeine

The decaffeinated extract is separated from the caffeine-containing spent solvent. Normally, separation is the result of the continuous removal of decaffeinated extract from one end of the decaffeination column and spent solvent from the other end of the column. For ethyl acetate as the solvent, the spent solvent stream usually contains from about 0.5 to about 2% by weight total solubles. The ratio of noncaffeine solubles to caffeine is typically about 2:1 by weight. For reasons previously noted, it is desirable to recover both the caffeine and noncaffeine solubles present in the spent solvent stream.

Preferably, this spent solvent stream is concentrated prior to caffeine removal to minimize the amount of solvent which must be handled and contacted with water for caffeine removal. In addition, concentration of the spent solvent permits maximization of mass transfer of caffeine to the water and reduces capital equipment requirements. Concentration can be effected by flashing off the spent solvent through the use of conventional thin film evaporators or the like. The evaporated solvent is typically condensed and recovered for reuse in further extract decaffeination. The spent solvent is typically concentrated to a total solubles content of from about 3 to about 8% by weight.

The spent solvent (concentrated or unconcentrated) is treated for removal of caffeine. Removal is achieved by contacting the spent solvent with water to partition the caffeine from the solvent phase into the aqueous phase. Substantially complete removal of caffeine from the spent solvent can be realized depending upon the amount of water employed and the nature of the particular solvent. Generally, a ratio of water-to-spent solvent of from about 0.3:1 to about 10:1 by weight is effective to partition caffeine into the aqueous phase. A preferred ratio in the case of a halogenated solvent such as methylene chloride is from about 5:1 to about 6:1 by weight. In the case of a nonhalogenated solvent such as ethyl acetate, the preferred ratio is from about 0.6:1 to about 1.4:1 by weight.

The purity of the water employed to remove the caffeine from the spent solvent can be important to processing efficiency. Typically, the water used is substantially pure. Examples of suitable purified water include those treated by reverse osmosis, deionization and distillation. Increasing the purity of the water increases the efficiency of caffeine removal from the spent solvent.

Another important factor in removing caffeine from the spent solvent is the difference in temperature between the spent solvent and the treatment water. Generally, the temperature of the water is lower than that of the spent solvent. A lower water temperature favors the transfer of caffeine from the spent solvent to the resulting aqueous phase. The greater the difference in temperature, the more favorable is the transfer of caffeine from the spent solvent to the aqueous phase. When ethyl acetate is used as the solvent, the temperature of the treatment water is from about 50° to about 80° F. while the temperature of the spent solvent is from about 100° to about 160° F.

The removal of caffeine from the spent solvent can be achieved by a number of art recognized liquid-liquid extraction techniques. Typically, this spent solvent decaffeination step is similar to that of the extract decaffeination step. For example, the spent solvent can be introduced into one end of a decaffeination column in a countercurrent fashion to water introduced into the other end of the column. The main difference is that the spent solvent moves as small dispersed droplets through a continuous aqueous phase. As in the case of the extract decaffeination step, removal of caffeine from the spent solvent can be facilitated by the use of conventional liquid-liquid contacting devices. These devices permit intimate contact between the water and the spent solvent with efficient recovery of both the caffeine-containing aqueous phase and the decaffeinated spent solvent phase.

The separated caffeine-containing aqueous phase or spent water typically has a total solubles content of from about 1 to about 4.5% by weight. For ethyl acetate as the solvent, caffeine and noncaffeine solubles are typically present in an approximately 1:1 by weight ratio. Also usually present in the spent water is a certain amount of residual solvent. Where ethyl acetate is used, the spent water typically contains from about 7 to about 9% by weight solvent. If desired, this solvent can be removed from the spent water through a desolventizing step.

Prior to solidification of the caffeine, it is usually necessary to further concentrate the caffeine present in the spent water. Caffeine normally has a relatively low solubility in water. However, it has been found that the solubility of caffeine in spent water is significantly greater. The following table gives some representative values for the solubility of caffeine in water containing differing levels of noncaffeine solubles:

TABLE 1

| % Noncaffeine Solubles | % Caffeine (75° F.) | % Caffiene (35° F.) |
|---|---|---|
| 0 | 2.1 | 0.1 |
| 5 | 7.4 | 3.6 |
| 10 | 9.2 | 6.2 |
| 15 | 9.9 | 7.4 |
| 20 | 10.3 | 7.5 |

The solubility of caffeine reaches a maximum at increasing concentrations of noncaffeine solubles. At 35° F., the solubility of caffeine reaches a maximum of about 7.5% by weight; at 75° F., the solubility of caffeine reaches a maximum of about 10.5% by weight.

The increased solubility of caffeine in spent water is believed to be due to the interaction of caffeine with compounds present in the noncaffeine solubles. It has been found that caffeine complexes with chlorogenic acid in about a 1:1 ratio. The caffeine-chlorogenic acid complex is more soluble in water than pure caffeine. Chlorogenic acid is one of the primary components present in the noncaffeine solubles of spent water. The complexing of caffeine with chlorogenic acid present in the noncaffeine solubles thus increases the solubility of caffeine in the spent water.

This solubility phenomena of caffeine in a spent water can have an impact on the amount of caffeine which can be removed from spent water at a given temperature. Normally, spent water contains a relatively low level of caffeine, e.g. about 2% or less by weight. Because of the caffeine solubility phenomena, the yield of caffeine from this spent water is usually well below about 50% by weight, even at lower temperatures. However, by concentrating the spent water, it has been found that the amount of caffeine removed at a given temperature can be significantly increased to about 50% by weight or more.

Usually, the spent water is concentrated to a caffeine content of from about 7 to about 30% by weight. The lower caffeine content limit represents a practical consideration based on the solubility phenomena of caffeine in spent water. The upper limit represents a practical consideration based on the increase in total solubles (caffeine and noncaffeine solubles) during concentration. As the total solubles content increases, the spent water becomes more viscous. When the caffeine is later solidified, it can be more difficult to separate the caffeine from the viscous residual spent water. More typically, the spent water is concentrated to a caffeine content of from about 15 to about 22% by weight.

Increasing the concentration of caffeine in the spent water does decrease the yield of noncaffeine solubles from the residual spent water upon solidification and separation of the caffeine. However, it has been found that the decreases in noncaffeine solubles recovered from the residual spent water is usually minimal, especially compared to the significant increase in caffeine removal. A more important concern is the need to protect against degradation or loss of flavor and aroma compounds present in the noncaffeine solubles. Conditions under which spent water is concentrated will thus be selected with an eye toward minimizing such degradation or loss while at the same time efficiently concentrating the spent water.

Concentration of the spent water is usually effected by evaporation. Thin film evaporation is usually an efficient means for concentrating the spent water. Besides concentrating the spent water, evaporation can be used to remove residual solvent. Evaporation of the spent water can usually be achieved by heating the spent water to a temperature of from about 120° to about 250° F. The temperature selected depends upon whether evaporation is conducted under a vacuum or at atmospheric pressure. Typically, steam is used as the heating medium. The above temperature range, especially in conjunction with a vacuum, is usually sufficient to efficiently evaporate the spent water while protecting against degradation or loss of flavor and aroma components present in the noncaffeine solubles.

Coffee extract and spent solvent evaporators can be utilized to concentrate spent water. A particularly suitable device for evaporating the spent water is a double effect evaporator. Basically, the double effect evaporator comprises two separate evaporators. In the first evaporator, the spent water is partially concentrated due to heating by a first lower temperature heating medium. Typically, the lower-temperature heating medium is vaporized water from the second evaporator. The partially concentrated spent water is then sent to a second evaporator for further concentration due to heating by a second higher-temperature heating medium. Typically, this higher-temperature heating medium is pressurized steam.

Concentrated spent water usually requires special handling, especially during storage. Where the total solubles concentration is high, e.g. about 40% or more by weight, there can be the problem of solubles precipitating out of the spent water. This problem can usually be solved by maintaining the spent water at a sufficiently high temperature prior to solidification and separation of the caffeine. Maintaining the spent water at a temperature of from about 140° to about 160° F. is usually sufficient. Agitation of the concentrated spent water can also help alleviate this problem.

After concentration, the caffeine present in the spent water is solidified. A number of suitable methods can be used to solidify caffeine. One such method is referred to as the "freeze-thaw" method. Concentrated spent water, when cooled to a temperature of about 32° F. or below, freezes or solidifies. When the frozen spent water is permitted to warm back up to a liquid state, a solid crystalline caffeine mass can be separated from the residual liquid. The noncaffeine solubles redissolve in the residual liquid while the crystalline caffeine preferentially remains in a solid state.

In the freeze-thaw method, the concentrated spent water is typically frozen at a temperature of about 0° F. or below. After freezing, the solidified spent water is warmed up to a temperature sufficient to permit separation of the crystalline caffeine from the residual liquid. Typically, the solidified spent water is warmed up to a temperature as high as about 70° F. While cooler temperatures as low as about 40° F. can be utilized to maximize caffeine yield, it usually requires several hours before the frozen spent water is fluid enough to permit effective separation of the crystalline caffeine. At temperatures of about 70° F., some of the crystallized caffeine redissolves in residual liquid which lowers the yield of caffeine. Thus, in the freeze-thaw method, faster processing conditions are balanced against a potentially lower yield of caffeine from the spent water.

Another method for solidifying caffeine in concentrated spent water is referred to as the "precipitation" method. Effective precipitation of caffeine depends upon the difference in solubility of the noncaffeine solubles and the caffeine at various temperatures. In the precipitation method, the concentrated spent water is cooled to a temperature as low as about 40° F. During cooling, the concentrated spent water is neither agitated nor seeded with cystalline caffeine. The caffeine precipitates out as an amorphous solid. The caffeine solid is then separated from the residual spent water which contains most of the noncaffeine solubles.

A preferred method for solidifying caffeine in the spent water is referred to as the "crystallization" method. Caffeine can crystallize as monohydrate crystals upon appropriate cooling. Crystallization of caffeine is more efficient from a processing standpoint than the freeze-thaw method. Crystallization also obtains a greater caffeine yield than the precipitation method. Usually, crystallization results in a yield of about 50% or more by weight of the caffeine from spent water. More typically, the caffeine yield in a crystallization method is from about 60 to about 70% by weight. Seeding of the spent water is unnecessary to induce nucleation of the caffeine crystals. It has been found that concentrated spent water forms seed crystals upon appropriate cooling.

Caffeine can crystallize in spent water at temperatures of about 80° F. or higher depending upon the concentration. However, because of decreasing solubility, it is generally advantageous to crystallize the caffeine at lower temperatures. Caffeine is usually crystallized from spent water at temperatures below about 50° F. A typical temperature range for crystallization of caffeine from the spent water is from about 35° to about 45° F.

A minimum crystallization residence time can be important to improving the yield of crystalline caffeine from the spent water. It has been found that a minimum residence time of at least about 0.25 hours (15 minutes) usually provides a suitable yield of crystallized caffeine (about 50% or more by weight). Once the crystallization residence time reaches about 1 hour, the yield of caffeine typically reaches a maximum.

Agitation of the spent water can also be important for the crystallization of the caffeine in the spent water. Crystallization of caffeine in spent water is very dependent on mass transfer. Agitation of spent water increases mass transfer which results in more frequent contact of caffeine molecules and faster crystal growth. Increasing the rate of agitation usually increases the rate of caffiene crystallization up to the point where the shear forces begin to destroy the crystals.

Crystallization can be carried out in a number of suitable devices which are referred to as crystallizers. The basic requirements are that the crystallizer include means for agitating the spent water and means for cooling the spent water to the desired temperature. Typically, the crystallizer is fitted with an impeller for agitation and a jacket for circulation of a cooling medium. Typical cooling media include chilled water, alcohol-water mixtures and ethylene glycol, along or usually mixed with water. An ethylene glycol-water mixture is a particularly suitable coolant for low temperature crystallization of caffeine from spent water.

Crystallization of caffeine can be conducted in a batch fashion. However, for processing efficiency, it is usually preferable to conduct a continuous crystallization. In continuous crystallization, cooled spent water can be introduced into the top of the crystallizer. The slurry of crystallized caffeine and spent water can then be removed from the bottom of the crystallizer. A sufficient residence time to permit effective crystallization of the caffeine can be achieved by adjusting the volume of spent water in the crystallizer.

After solidification, the caffeine is then separated from the residual spent water or filtrate. A suitable separation technique from the standpoint of processing efficiency involves centrifuging the caffeine solids from the filtrate. A suitable centrifuge is a basket-type centrifuge which contains a cylindrical basket having a multiplicity of spaced holes or apertures therein. Caffeine is collected as a cake on the inside of the basket. A filtering medium can be used to cover the inner wall of the basket to collect the cake. As the centrifuge rotates at high speed, the filtrate is forced through the holes in the basket (and through the optional filtering medium). The filtrate is then collected for recovery of the noncaffeine solubles contained therein. Other devices such as rotary drum filters can also be utilized to separate the caffeine from the filtrate.

When crystallized caffeine is separated in a centrifuge, the resulting caffeine forms a porous mass. As a result, the filtrate containing the noncaffeine solubles passes easily through the caffeine cake even as the thickness increases. The main limitation on caffeine cake thickness is the capacity of the centrifuge. However, sometimes more of the noncaffeine solubles precipitate out of the spent water along with the caffeine during crystallization. These precipitated noncaffeine solubles can decrease the porosity of the resulting caffeine cake which inhibits the ability of the filtrate to pass through. Typically, the cake in such circumstances has a much browner or tanner color.

This problem of excessive precipitation of noncaffeine solubles is believed to be the result of oxidation products of unknown chemical composition which are formed during the step of evaporating the spent water. There are three methods for overcoming this problem. In one method, the spent water is concentrated by evaporation under a vacuum. Evaporation can be conducted under a vacuum of at least about 5 inches of mercury. Typically, evaporation is conducted under a vacuum of from about 7 to about 28 inches of mercury. Evaporation under a vacuum also helps preserve flavor and aroma components present in the noncaffeine solubles due to the decrease in time and temperature required to sufficiently concentrate the spent water.

The second method involves evaporation of the spent water in an inert gas atmosphere. Suitable inert gases include nitrogen and carbon dioxide.

The third method involves adjustment of the pH of the spent water. When the pH of the spent water, which is typically about 4, is adjusted to about 7 or above, the precipitation problem is overcome. The pH is adjusted by adding alkaline materials. These alkaline materials inclued potassium hydroxide, sodium hydroxide, sodium carbonate and sodium bicarbonate. Once the crystallized caffeine is separated, the residual spent water can be adjusted to the desired acidic pH by the addition of acidic materials such as hydrochloric acid.

Recovery of Noncaffeine Solubles

The filtrate usually contains about 80% or more of the original noncaffeine solubles present in the spent water. The filtrate also contains a significant amount of caffeine. The total solids content of the filtrate can range from about 25 to about 35% by weight. The ratio of noncaffeine solubles to caffeine can range from about 2:1 to about 4:1 by weight. Typically, the filtrate contains about 32% total solids and a ratio of noncaffeine solubles to caffeine of about 3:1 by weight.

After separation of the solidified caffeine, the noncaffeine solubles present in the filtrate can be recovered. As used herein, the term "recovery of noncaffeine solubles" refers to a method by which these noncaffeine solubles present in the filtrate are eventually included in a decaffeinated or nondecaffeinated instant coffee product. For example, the filtrate containing the noncaffeine solubles can be dried and the powder formed blended with other instant coffee products. The filtrate can also be added to a coffee extract which is processed further to form an instant coffee product. Due to the high level of caffeine present, it is desirable to blend only a small portion of the filtrate with a nondecaffeinated instant coffee product or a nondecaffeinated coffee extract.

Because of this high caffeine content, the filtrate is usually added back to coffee extract to be decaffeinated. The ratio of filtrate to coffee extract usually ranges from about 1 to about 10% on a solids basis. More typically, the raito is from about 2 to about 5% on a solids basis. Addition of the filtrate to the coffee extract to be decaffeinated insures the recovery of about 90% or more of the caffeine in the entire decaffeination system.

The recovery of noncaffeine solubles from the filtrate is particularly useful in combination with the process described in Belgium Patent No. 865,488 to Bolt et al, issued Oct. 2, 1978 (herein incorporated by reference). In the process of the Bolt et al patent, the noncaffeine solubles present in the decaffeinated spent solvent are eventually added to the decaffeinated extract. Typically, the decaffeinated spent solvent is combined with the decaffeinated extract from the extract decaffeination column. This solvent/decaffeinated extract mixture is usually sent to a flash evaporator to remove some of the solvent. The partially desolventized mixture is then sent to an extract stripper to remove the remainder of the residual solvent. Any condensed voltiles stripped from the roast coffee extract prior to decaffeination can then be added to the desolventized decaffeinated extract. The resulting decaffeinated extract is then dried to form a decaffeinated instant coffee product such as by spray drying or freeze drying, with or without a concentration step prior to addback of the condensed volatiles.

Additional noncaffeine solubles can be recovered from the caffeine cake. Usually, this caffeine cake is from about 85 to about 95% pure caffeine (dry basis). The remaining 5 to 15% solids are noncaffeine solubles usually adhering to the surface of the cake. These adherent noncaffeine solubles can be recovered by first redissolving the cake in water. The caffeine is then recrystallized from the aqueous solution to form a purer cake. The recrystallization liquor which contains dissolved noncaffeine solubles is collected and typically added to the filtrate which is then added back to the coffee extract to be decaffeinated.

Another method for recovering the adherent noncaffeine solubles is to water wash the caffeine cake. The wash water-to-caffeine cake ratio can range from about 0.3 to about 1.5 by weight. As the ratio of water to cake increases, the amount of noncaffeine solubles in the wash liquor also increases. However, an increase in the ratio also increases the amount of caffeine which is redissolved in the wash liquor. Cooler wash temperatures are also favored. The wash water temperature can range from about 35° to about 70° F. More typically, the wash water temperature is from about 35° to about 45°

F. A preferred ratio of wash water to caffeine cake is about 0.6 to about 0.8 by weight at the preferred wash water temperature of from about 35° to about 45° F.

BRIEF DESCRIPTION OF THE DRAWING

The FIGURE represents a flow diagram of a preferred embodiment of the spent water recovery system of the present invention.

EXAMPLE OF A PREFERRED SPENT WATER RECOVERY SYSTEM ACCORDING TO THE PRESENT INVENTION

The FIGURE represents a flow diagram of a preferred spent water recovery system according to the present invention. Referring generally to the FIGURE, roast coffee extract and water-immiscible organic solvent such as ethyl acetate enter at one end of the system. At the other end of the system, caffeine and final decaffeinated extract are obtained as the products.

Referring more specifically to the FIGURE, roast coffee extract having a total solids content of from about 16 to about 30% by weight and a temperature of about 150° F. is pumped into the top of the primary (first) decaffeination column. Ethyl acetate at a temperature of about 50° F. is pumped into the bottom of the column. The primary decaffeination column has an impeller which rotates at about 10 to about 100 rpm. The ethyl acetate-to-extract ratio entering the column ranges from about 1.4:1 to about 2:1 by weight. The extract and ethyl acetate pass countercurrently and are mixed by the rotating impeller. Caffeine-containing spent solvent exits at the top of the column while (initial) decaffeinated extract exits at the bottom of the column.

The spent solvent from the primary decaffeination column has a total solubles content of about 0.5 to about 2% by weight. The spent solvent is concentrated in a thin film solvent evaporator to a total solubles content of from about 3 to about 8% by weight at atmospheric pressure. The evaporated ethyl acetate is collected as recovered solvent and recycled back to the primary decaffeination column.

The concentrated spent solvent at a temperature of about 140° F. is then pumped into the bottom of a secondary (second) decaffeination column. Process water at a temperature of about 50° F. is pumped into the top of the column. The process water-to-concentrated spent solvent ratio ranges from about 0.6:1 to about 1.4:1 by weight. The secondary decaffeination column has an impeller which rotates at about 10 to about 100 rpm. The concentrated spent solvent and process water move countercurrently and are mixed by the rotating impeller. Decaffeinated spent solvent is obtained at the top of the column while caffeine-containing spent water is obtained at the bottom of the column.

The decaffeinated spent solvent is combined with the initial decaffeinated extract and is then sent to a flash evaporator. In the flash evaporator, some of the ethyl acetate solvent is evaporated, collected as recovered solvent and recycled to the primary decaffeination column. The partially desolventized decaffeinated extract is then sent to an extract stripper. The stripper removes the residual ethyl acetate solvent which is collected as recovered solvent and recycled back to the primary decaffeination column. The substantially desolventized (final) decaffeinated extract is then sent to further instant coffee processing steps such as concentration and spray drying to form a decaffeinated instant coffee product.

The spent water obtained from the secondary decaffeination column contains about 1 to about 4.5% by weight total solubles (about a 1:1 by weight ratio of caffeine to noncaffeine solubles), plus about 7 to about 9% by weight ethyl acetate solvent. The spent water is sent to a spent water evaporator to concentrate the spent water to a total solubles content of about 38 to about 42% by weight (about half by weight being caffeine) and to remove the residual solvent. The spent water evaporator is a double effect evaporator. In the first evaporator, the spent water is evaporated by heating with vaporized water from the second evaporator. After partial concentration in the first evaporator, the spent water enters the second evaporator where further concentration occurs due to heating by about 10 to about 20 psig steam.

The concentrated spent water at a temperature of about 70° F. is then sent to a crystallizer having an impeller which rotates at about 20 rpm or less. The crystallizer further includes a jacket through which an ethylene glycol-water mixture circulates at a temperature of about 32° F. The temperature within the crystallizer ranges from about 35° to about 45° F. The slurry of crystallized caffeine and spent water is pumped from the bottom of the crystallizer into a basket centrifuge. Crystallized caffeine collects as a porous cake in the basket as the centrifuge rotates. The filtrate is collected and then blended with the roast coffee extract going to the primary decaffeination column at a ratio of about 3% on a solids basis.

The spent water recovery system shown in the FIGURE insures the eventual return of most of the noncaffeine solubles to the decaffeinated extract, as well as recovery of most of the caffeine as a valuable by-product. As the system intially starts up, the level of non-caffeine solubles and caffeine increases in the spent water. However, as the system approaches steady state operation, the noncaffeine solubles eventually end up in the final desolventized decaffeinated extract because the filtrate is recycled back to the coffee extract to be decaffeinated. The caffeine present in the spent water eventually leaves as caffeine cake after the crystallization and centrifuging step.

What is claimed is:

1. A decaffeination process which recovers 90% or more of the caffeine from a coffee extract, which comprises the steps of:
(a) contacting roast coffee extract with ethyl acetate solvent to form decaffeinated extract and a caffeine-containing solvent phase;
(b) contacting the caffeine-containing solvent phase with water to form an aqueous caffeine-containing phase and a decaffeinated solvent phase;
(c) crystallizing caffeine in the aqueous phase by cooling the aqueous phase, concentrating the aqueous phase, or a combination thereof;
(d) separating the crystallized caffeine from the residual aqueous phase; and
(e) recovering noncaffeine solubles from the residual aqueous phase in an amount of about 80% or more based on the non-caffeine solubles present in the aqueous caffeine-containing phase of step (b), by adding the residual aqueous phase to the coffee extract of step (a).

2. A decaffeination process according to claim 1 wherein said crystallization step comprises cooling the aqueous phase to a temperature below about 50° F. to crystallize out caffeine.

3. A decaffeination process according to claim 2 wherein said separation step comprises centrifuging the crystallized caffeine from the residual aqueous phase.

4. A decaffeination process according to claim 1 wherein said crystallization step is continuous.

5. A decaffeination process according to claim 1 the crystallization step comprising concentrating the aqueous phase to a caffeine content of from about 7 to about 30% by weight.

6. A decaffeination process according to claim 5 wherein the concentrated aqueous phase has a caffeine content of from about 15 to about 22% by weight.

7. A decaffeination process according to claim 5 wherein said concentration step comprises evaporating the aqueous phase.

8. A decaffeination process according to claim 7 wherein said evaporation step is conducted under a vacuum.

9. A decaffeination process according to claim 1 comprising the further step of adding noncaffeine solubles from the decaffeinated ethyl acetate solvent phase of step (b) to the decaffeinated extract of step (a).

10. In a decaffeination process which recovers about 90% or more of the caffeine from coffee wherein roast coffee extract is contacted with ethyl acetate solvent to form decaffeinated extract and a caffeine-containing solvent phase and wherein the caffeine-containing solvent phase is contacted with water to form an aqueous caffeine-containing phase and a decaffeinated solvent phase, a method for recovering noncaffeine solubles from the aqueous phase which comprises the steps of:
(a) concentrating the aqueous phase to a caffeine content of from about 7 to about 30% by weight;
(b) crystallizing caffeine out of the concentrated aqueous phase;
(c) separating the crystallized caffeine from the residual aqueous phase; and
(d) recovering noncaffeine solubles from the residual aqueous phase in an amount of 80% or more based on the noncaffeine solubles present in the aqueous caffeine-containing phase which is concentrated in step (a) by recycling noncaffeine solubles from the residual aqueous phase to a roast coffee extract to be decaffeinated.

11. A decaffeination process according to claim 10 wherein said crystallization step comprises cooling the aqueous phase to a temperature below about 50° F. to crystallize out caffeine.

12. A decaffeination process according to claim 10 wherein the concentrated aqueous phase has a caffeine content of from about 15 to about 22% by weight.

13. A decaffeination process according to claim 12 wherein said concentration step comprises evaporating the aqueous phase.

14. A decaffeination process according to claim 13 wherein said evaporation step is conducted under a vacuum.

15. A decaffeination process according to claim 10 wherein said separation step comprises centrifuging the crystallized caffeine from the residual aqueous phase.

16. A decaffeination process according to claim 10 wherein said crystallization step is continuous.

17. In a decaffeination process which recovers about 90% or more of the caffeine from coffee, and which includes the steps of contacting roast coffee extract with ethyl acetate solvent to form decaffeinated extract in a caffeine-containing solvent phase; contacting the caffeine-containing solvent phase with water to form a aqueous caffeine-containing phase and a decaffeinated solvent phase; and adding noncaffeine solubles from the decaffeinated solvent phase to the decaffeinated extract; the improvement which comprises the steps of:

(a) concentrating the aqueous phase to a caffeine content of from about 15% to about 22% by weight;
(b) cooling the concentrated aqueous phase to a temperature of from about 35° to about 45° F. for at least about 0.25 hours to crystallize out caffeine;
(c) separating crystallized caffeine from the residual aqueous phase; and
(d) recovering noncaffeine solubles from the residual aqueous phase in an amount of 80% or more based on the non-caffeine solubles present in the aqueous caffeine-containing phase which is concentrated in step (a) by recycling noncaffeine solubles from the residual aqueous phase to a roast coffee extract to be decaffeinated.

18. A decaffeination process according to claim 17 wherein said concentration step comprises heating the aqueous phase to a temperature of from about 120° to about 250° F.

19. A decaffeination process according to claim 17 wherein the aqueous phase is evaporated under a vacuum of from about 7 to about 28 inches of mercury.

20. A decaffeination process according to claim 17 wherein the cooled aqueous phase is held at a temperature of from about 35° to about 45° F. for from about 0.25 to about 1 hour.

21. A decaffeination process according to claim 20 wherein said separation step comprises centrifuging the crystallized caffeine from the residual aqueous phase.

22. A decaffeination process according to claim 17 wherein the noncaffeine solubles from the residual aqueous phase are added to the coffee extract at a ratio of from about 2 to about 5% on a solids basis.

* * * * *